United States Patent [19]

Christensen

[11] 4,179,499

[45] Dec. 18, 1979

[54] PESTICIDES FOR SNAILS

[75] Inventor: Kresten Christensen, Brig, Switzerland

[73] Assignee: Lonza Ltd., Gampel, Switzerland

[21] Appl. No.: 618,361

[22] Filed: Oct. 1, 1975

Related U.S. Application Data

[63] Continuation-in-part of Ser. No. 515,473, Oct. 17, 1974, abandoned, and a continuation-in-part of Ser. No. 515,603; Oct. 17, 1974, abandoned.

[30] Foreign Application Priority Data

Jul. 5, 1974 [CH] Switzerland ............... 009310/74
Jul. 8, 1974 [CH] Switzerland ............... 009369/74

[51] Int. Cl.$^2$ ............... A01N 11/04; A01N 9/22; A01N 9/02
[52] U.S. Cl. ............... 424/143; 424/274; 424/324
[58] Field of Search ............... 424/10, 17, 23, 84, 424/333, 324, 143

[56] References Cited

U.S. PATENT DOCUMENTS

| | | | |
|---|---|---|---|
| 1,204,794 | 11/1916 | Levy ............... | 424/10 |
| 1,893,008 | 1/1933 | Wamoscher ............... | 424/10 |
| 3,074,845 | 1/1963 | Geary ............... | 424/23 |
| 3,137,618 | 1/1964 | Pearce ............... | 424/23 |
| 3,274,052 | 9/1966 | Yaffe et al. ............... | 424/23 |

FOREIGN PATENT DOCUMENTS 510399  9/1971  Switzerland ............... 424/78
619705  3/1949  United Kingdom ............... 424/333

*Primary Examiner*—Frederick E. Waddell
*Attorney, Agent, or Firm*—Fisher, Christen & Sabol

[57] ABSTRACT

A pesticide composition for snails which includes a binder, at least one bait substance, a snail pecticide and expanded perlite, which is a carrier. The expanded perlite is present as granules in an amount between 30 to 70 percent by weight based on the total weight of the pesticide composition. The snail pesticide is substantially located on the surface of the expanded perlite and is attached to the surface of the expanded perlite by means of the binder. The perlite is in its expanded form and is in a substantially spheroidal shape having a uniformly rough surface. Preferably the binder is wheat starch. Preferably the pesticide is metaldehyde. A process for the production of a pesticide composition for snails which includes adhering at least one bait substance and a snail pesticide by means of a binder to expanded perlite.

A further pesticide composition for snails which includes a binder, at least one bait substance, a snail pesticide, a carrier, and least one amide having the formula:

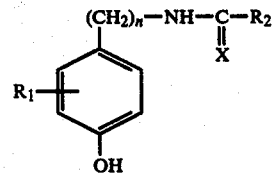

wherein X is an oxygen atom or a sulfur atom, n is 0 or 1, $R_1$ is —OH or —OCH$_3$ and $R_2$ is an alkyl group having 5 to 11 carbon atoms, or an alkylene group having 5 to 11 carbon atoms, or an alkyl group having 5 to 11 carbon atoms and being substituted with a phenyl group or a phenyl group substituted with one to three alkyl groups, each such alkyl group having one to five carbon atoms, or an alkylene group having 5 to 11 carbon atoms and being substituted with a phenyl group or a phenyl group substituted with one to three alkyl groups, each such alkyl group having one to five carbon atoms. The amide irritates the mucous membrane of warm-blooded animals and prevents them from picking up and eating the pesticide composition. A process of preparing such pesticide composition.

15 Claims, No Drawings

PESTICIDES FOR SNAILS

This application is a continuation-in-part application of U.S. Ser. No. 515,473, filed on Oct. 17, 1974, now abandoned and is a continuation-in-part application of U.S. Ser. No. 515,603, filed on Oct. 17, 1974 now abandoned.

BROAD DESCRIPTION OF THIS INVENTION

1. Field of this Invention

This invention relates to a pesticide composition for snails.

2. Prior Art

It is known to produce pesticide compositions for snails from certain carrier substances which contain binders, bait substances and active components (i.e., pesticides). See Swiss Pat. No. 510,399. That patent uses, as carrier substances, fine bran and vermiculite. These known pesticide compositions for snails have the disadvantage that they are also picked up easily and eaten by warm blooded creatures, which leads to serious, mostly deadly, poisonings. Hedgehogs and dogs are particularly endangered. Vermiculite has the disadvantage that the bait substances and active substances cannot be distributed uniformly on the surface of vermiculite because of the form of the vermiculite grain, which is divided into layers. Moreover the vermiculite grains are very brittle, so that during production many small grains develop which have no pesticide effect or have only a very much reduced pesticide effect. Brain is the broken coat of cereal grain, separated from the flour or meal by sifting or bolting. Bran is irregular in shape.

See also U.S. Pat. No. 3,074,845, British Pat. No. 619,705, U.S. Pat. No. 3,137,618, U.S. Pat. No. 3,274,052, U.S. Pat. No. 1,893,008 and U.S. Pat. No. 1,204,794.

BROAD DESCRIPTION OF THIS INVENTION

An object of this invention is to provide a novel pesticide composition for snails which completely or nearly completely eliminates the danger of poisoning to warm blooded animals such as dogs and hedgehogs, and which is very effective against snails. A further object of this invention is to provide a novel pesticide compositions for snails which can be made without the production of wasteful small grains or particles and which reduces the amount of pesticides that is used in the pesticide composition without reducing the effectiveness of the pesticide against snails. Another object of this invention is to provide a novel process for preparing such a novel pesticide composition. Other objects and advantages of this invention are set forth elsewhere herein or are obvious to one ordinarily skilled in the art from the disclosure of this application.

Such objects and advantages are achieved or possessed, respectively, by this invention.

The first embodiment of this invention involves a pesticide composition for snails which include a binder, at least one bait substance, a snail pesticide, a carrier and at least one amide having the formula:

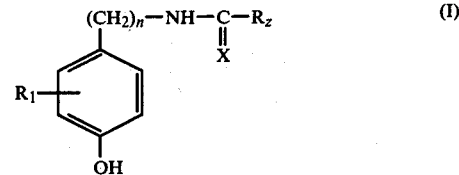

wherein X is an oxygen atom or a sulfur atom, n is 0 or 1, $R_1$ is —OH or —OCH$_3$, and $R_2$ is an alkyl group having 5 to 11 carbon atoms, or an alkylene group having 5 to 11 carbon atoms, or an alkyl group having 5 to 11 carbon atoms and being substituted with a phenyl group or a phenyl group substituted with one to three alkyl groups, each such alkyl group having one to five carbon atoms, or an alkylene group having 5 to 11 carbons and being substituted with a phenyl group or a phenyl group substituted with one to three alkyl groups, each such alkyl group having one to five carbon atoms. The amide irritates the mucous membrane of warm-blooded animals and prevents them from picking up and eating the pesticide composition. Preferably the amine is present in an amount between 0.005 and 5 percent by weight based on the total weight of the pesticide composition. Preferably the amine is nonyl acid vanillyl amide. Preferably the carrier is expanded perlite, and preferably the expanded perlite is present as granules in an amount between 30 and 70 percent by weight based on the total weight of the pesticide composition. The snail pesticide is substantially located on the surface of the expanded perlite and is attached to the surface of the carrier by means of the binder.

The first embodiment of this invention also involves a process which includes admixing at least one amide of formula I with at least one bait surface, a binder, a carrier and a snail pesticide, or which includes applying at least one amide of formula I to the surface of a composition comprised of at least one bait substance and a snail pesticide adhered to a carrier by means of a binder.

The second embodiment of this invention involves a pesticide composition for snails which includes a binder, at least one bait substance, a snail pesticide and expanded perlite, which is a carrier. The expanded perlite is preferably present as granules in an amount between 30 and 70 percent by weight based on the total weight of the pesticide composition. The snail pesticide is substantially located on the surface of the expanded perlite and is attached to the surface of the expanded perlite by means of the binder. The perlite is in its expanded form and is in a substantially spheroidal shape having a uniformally round surface. Preferably the binder is wheat starch. Preferably the pesticide is metaldehyde.

The second embodiment of this invention also involves a process for the production of a pesticide composition for snails which includes adhering at least one bait substance and a snail pesticide by means of a binder to expanded perlite. Preferably the adhering step was achieved by admixing together the bait substance, the expanded perlite, the pesticide and the binder.

DETAILED DESCRIPTION OF THIS INVENTION

In the amide of formula I, $R_1$ can be —OH or —CH$_3$, $R_2$ can be an alkyl group having 5 to 11 carbon atoms or an alkylene group having 5 to 11 carbon atoms or an alkyl group having 5 to 11 carbon atoms which is substituted with an aryl group or an alkylene group having 5 to 11 carbon atoms substituted with an aryl group, n can be 0 or 1 and X can be an oxygen atom or a sulfur atom. The preferred amide of formula I is nonyl acid vanillyl amide.

Examples of $R_2$ when $R_2$ is an alkyl group are 1-pentyl, 2-methyl-1-butyl, neopentyl, 2-pentyl, 3-methyl-1-butyl, 3-pentyl, 3-methyl-2-butyl, 1-hexyl, 2-hexyl, 2-methyl-2-butyl, 2-ethyl-1-butyl, 2-methyl-1-pentyl, 3,3-dimethyl-1-butyl, 3-methyl-1-pentyl, 2,3-dimethyl-1-butyl, 4-methyl-1-pentyl, 3-hexyl, 3-methyl-2-pentyl, 2,2-dimethyl-2-butyl, 4-methyl-2-pentyl, 2,3-dimethyl-2-butyl, 2-methyl-3-pentyl, 2,4-dimethyl-3-pentyl, 2-methyl-2-pentyl, 2,4-dimethyl-1-pentyl, 3-methyl-3-pentyl, 2,3,3-trimethyl-2-butyl, n-heptyl, 1-octyl, 2-octyl, 2,3,4-trimethyl-1-pentyl, 2,4,4-trimethyl-1-pentyl, nonyl, decyl and undecyl.

Examples of $R_2$ and $R_2$ is an alkylene group are 1-pentyl, 2-pentenyl, 3-pentenyl, 2-methyl-1-butenyl, 1-hexenyl, 3-methyl-1-butenyl, 2-hexenyl, 3-methyl-2-butenyl, 3-hexenyl, 2-methyl-2-butenyl, 2-ethyl-1-butenyl, 2-methyl-1-pentenyl, 3,3-dimethyl-1-butenyl, 3-methyl-1-pentenyl, 2,3-dimethyl-1-butenyl, 4-methyl-1-pentenyl, 2,2-dimethyl-2-butenyl, 3-methyl-2-pentenyl, 2,3-dimethyl-2-butenyl, 4-methyl-2-pentenyl, 2-4-dimethyl-3-penteny, 2-methyl-3-pentenyl, 2,4-dimethyl-1-pentenyl, 2-methyl-2-pentenyl, n-heptenyl, 3-methyl-3-pentenyl, 1-octenyl, 2,3,3-trimethyl-2-butenyl, 2-octenyl, 2,3,4-trimethyl-1-pentenyl, nonenyl, decenyl, 2,4,4-trimethyl-1-pentenyl and undecenyl.

Examples of $R_2$ when $R_2$ is a phenyl group substituted with one to three alkyl groups, each having one to five carbon atoms, are 2,3-dimethyl-phenyl, 2-methyl-phenyl, 2,6-dimethyl-phenyl, 3-methyl-phenyl, 3,5-dimethyl-phenyl, 4-methyl-phenyl, 2,4-dimethyl-phenyl, 2-ethyl-phenyl, 2,5-dimethyl-phenyl, 3-ethyl-phenyl, 3,4-dimethyl-phenyl, 4-ethyl-phenyl, 2,4,6-trimethyl-phenyl, 2-butyl-phenyl, 2,3,5-trimethyl-phenyl, 3-butyl-phenyl, 2,4,5-trimethyl-phenyl, 4-butyl-phenyl, 2,3,4-trimethyl-phenyl, 2-isopropyl-phenyl, 2-pentyl-phenyl, 3-isopropyl-phenyl, 4-pentyl-phenyl, 4-isopropyl-phenyl, 2,6-diethyl-phenyl, 2-propyl-phenyl, 2,5-diethyl-phenyl, 3-propyl-phenyl, 2,5-dibutyl-phenyl and 4-propyl-phenyl. Such alkyl groups can be methyl, ethyl, 1-propyl, 2-propyl, 1-butyl, 2-butyl, 2-methyl-1-propyl, tertiary butyl, 1-pentyl, 2-methyl-1-butyl, neopentyl, 3-methyl-1-butyl, 2-pentyl, 3-methyl-2-butyl, 3-pentyl and 2-methyl-2-butyl.

The amide of formula I irritates the mucous membranes of warm-blooded creatures and thereby keeps the warm-blooded animals from eating the pesticide composition for snails. The quantity of the amide of formula I is between 0.005 and 5 percent by weight of the total weight of the pesticide composition for snails. The substances encompassed by formula I irritate the mucous membrane. Examples of the substances of formula I and nonyl acid vanillyl amide (preferred), nonylene acid vanillyl amide, capsaicin, etc. The substances irritating the mucous membrane can be in the pesticide composition for snails of this invention in the form of a powder or a emulsion, or can be used in a solution, or can merely be applied to the surface. In the most preferred embodiment the substance irritating the mucous membrane of warm blooded creatures is used together with expanded perlite as the carrier material. The amides of Formula I have the advantage of preventing completely or nearly completely the packing up and eating of the pesticides compositions for snails by warm-blooded creatures, and yet do not limit in any way the snail killing effect of the pesticide composition.

The amides of formula I are well known—see, for example: Rompp Chemie-Lexikon, 7th Edition, Vol. 1, (1972), p. 496; Rompp Chemie-Lexikon, 6th Edition, Vol. 1, (1966), p. 927; Beilsteins Handbuch der organischen Chemie, EI, Vol. 13, pp. 322 and 323; Beilsteins Handbuch der organischen Chemie, E II, Vol. 13, p. 482; Arzneimittel-Forschung, Vol. 1, (1951), pp. 305–309; and Arzneimittel-Forschung, Vol. 15, (1969), pp. 718–727.

Any of the known active agents or pesticides for snails can be used. Examples of such pesticides are metaldehyde (prefered) copper(II) sulfate, kainite, phenol pentabromide, sodium pentachlorophenolate, 2,4,6-triiodophenol, and 2,4,6-tribromophenol.

Any bait substances (liquid or solid) for snails can be used. Examples of such bait substances are commercial feed substance, such as, ground grains, coarse meal soy beans, meat meal, fish meal, molasses, etc., or an aromatic agent, for example, anise or anise oil, which exerts a luring appeal on snails.

Any useful binder can be used. Examples of such binders are usually what are termed edible binders, such as, wheat starch (preferred), gum arabic, corn starch, potatoe starch, other starches, etc.

The carrier can be any known carrier used in snail pesticide compositions or the like when the amide (I) is included in the snail pesticide compositions. Examples of the carrier are pumice, a fine bran and vermiculite, and the preferred carrier is expanded perlite. Expanded perlite must be used as the carrier when the amide(I) is not used in the snail pesticide compositions.

Perlite is a form of volcanic rock, i.e., a glassy rhyolite varying in texture from porphyrtic to glassy gray with a pearly luster. Expanded perlite has a concentric shelly structure. When expanded perlite is crushed and carefully heated to high temperatures it expands to a lightweight cellular material 10 to 20 times its original volume, resembling rock wool in texture. Expanded perlite granules are substantially spheroid in shape and have a uniformly rough shape. Such allows a uniform and precise distribution of the bait substance(s) and active substance(s) on the expanded perlite granules. The expanded perlite granules are more crackproof than vermiculite and it results in a homogeneous grain size in the final product. The expanded perlite granules have the advantage that the pesticide is distributed substantially only on its surface and thus the entire amount of pesticide is potentially effective. Whereas in the case of the known snail grain granules, and in the other embodiments of this invention using known carriers, the pesticide is distributed in the entire grain. Since only the pesticide in the outside part of the known snail grain granules, etc., is potentially effective, a large part of it thus will be lost against snails. By using less pesticide, the expanded perlite granule embodiment of this invention makes snail pesticide grains less poisonous to warm blooded animals in the unlikely case of consumption thereof by warm blooded animals. In addition, it has been found that the expanded perlite snail granules (product) are much less dangerous for warm-blooded creatures, for example, hedgehogs or dogs, than the customary snail granules made of a bait substance, binder and metaldehyde (6 percent). This is so even in the case of double the percentage by weight content of metaldehyde (12 percent) in the pesticide compositions of this invention. Bran is the broken coat of cereal grain, separated from the flour or meal by sifting or bolting. Bran is irregular in shape. Pumice is a kind of volanic glass that is light and full of minute cavities. Vermiculite is a micaceous mineral, such as, kerrite, maconite, etc., which is a hydrous silicate derived generally from the alteration of some kind of mica. Vermiculite has the disadvantage that the bait substances and active substances cannot be distributed uniformly on the surface of vermiculite because of the form of the vermiculite grain, which is divided into layers. Moreover the vermiculite grains are very brittle, so that during production many small grains develop which have no pesticide effect or have only a very much reduced pesticide effect.

The carrier is used in an amount of 30 to 70 percent by weight of the pesticide composition.

As used herein all percentages, parts and properties are on a weight basis, unless otherwise stated or obvious to one ordinarily skilled in the art.

EXAMPLE 1

A snail grain was produced by applying metaldehyde (275 gm), wheat starch (375 gm), corn meal (650 gm) and expanded perlite granules (1.0 kg). A part of these snail grains were sprayed with enough of an alcoholic solution of nonyl acid vanillyl amide so that the grains contained 0.15 percent by weight of nonyl acid vanillyl amide. The snail grains (with and without nonyl acid vanillyl amide) were then examined in a laboratory test for their snail killing effect.

TABLE 1

The effect of snail grains with and without nonyl acid vanillyl amide
4 × 15 snails (Arion rufus and Deroceras reticulatus) per grain variation

| Variety of grain | Percent of dead snails after 104 hours |
| --- | --- |
| Snail grains without nonyl acid vanillyl amide | 80 |
| Snail grains with 0.15% nonyl acid vanillyl amide | 79 |

Therefore, it is clear that nonyl acid vanillyl amide has no adverse influence on the snail killing effect.

Snail grains with various concentrations of nonyl acid vanillyl amide were investigated in an experiment with dogs for their repellent effect. The results of these tests are clear from Table 2. The experiment was carried out with five male and five female Beagle hounds. The snail grain preparations were offered to the dogs always after two days of withdrawal of food, without adding any food. The intake of the preparations, the findings of their general condition and of their behavior as well as possible findings after dissection were established. In addition the picking up of food and the development of the body weight was also included. In order to avoid a wrong evaluation in the sense of "snail grain X was not eaten," dogs and preparation were assigned to each other temporarily according to a special scheme. The evaluation "snail grain X was not eaten" was based on the examination of the pertinent preparation in four to five tests, each of which was carried out with a different dog; in the case of one of these tests, a dog was always used that had never previously had any contact with a snail grain preparation. It turned out besides that dogs which had not picked up a snail grain preparation offered to them, later ate another one. The preparations were offered starting in the morning. If it was noticed in the course of the day that a dog had eaten snail grain, the remaining material (total quantity offered per dog was 100 gm) was withdrawn from him.

TABLE 2

The results of repellent tests with commercial snail grains and with perlite grains, with and without nonyl acid vanillyl amide

| Variety of snail grain | No of times offered | No of times eaten |
| --- | --- | --- |
| Commercial (metaldehyde 6%) | 1 | 1* |
| Perlite grain (metaldehyde 12%) without nonyl acid vanillyl amide | 7 | 4 |
| Perlite grain (metaldehyde 12%) with 0.01% nonyl acid vanillyl amide | 8 | 0 |
| Perlite grain (metaldehyde 12%) with 0.15% nonyl acid vanillyl amide | 6 | 0 |

Note:
*The dog had picked up a lethal dosage.

These experiments showed that pesticides for snails treated according to this invention were no longer picked up by warm blooded creatures and thus there was no longer any danger of poisoning.

EXAMPLE 2

A pesticide composition for snails in the form of granules (snail grains) was produced by application of a bait substance (corn meal) and a pesticide or active component (metaldehyde) by means of a binder (wheat starch) onto expanded perlite granules (the carrier). The composition was: expanded perlite granules, 1.0 kg; corn meal, 650 gm; wheat starch, 375 gm; and metaldehyde, 275 gm.

EXAMPLE 3

The effect of snail grains with perlite as the carrier as compared with similar preparation but which have vermiculite and fine bran as the carrier.

4×15 snails (Arion refus and Deroceras reticulatus) per grain variation

| Variety of grain | Percent of dead snails after 104 hours |
| --- | --- |
| Snail grains with perlite | 82.5 |
| Snail grains with vermiculite | 75.0 |
| Snail grains with fine bran | 50.0 |

It is clear, therefore, that expanded perlite as a carrier material has no adverse influence on the snail killing action (but does allow a more effective use of the snail pesticie). Snail grains with various carriers were than investigated for their repellant effect in an experiment with dogs. The results of these tests are clear from Table 4. The examination was conducted with five male and five female Beagle hounds. The snail grain preparations were offered to the dogs always following two days of withdrawal of food, without any addition to the food. The reception of these preparations, findings with regard to the general condition of the behavior of the animals as well as possible findings after dissecting were established. Moreover the acceptance of the food and development of the body weight were also included.

In order to avoid a misjudgment in the sense of "snail grain X was not eaten," dogs and preparations were assigned to each other temporarily according to a special scheme. The evaluation "snail grain X was not eaten" was based on the examination of the pertinent preparation in four to five tests, each of which was carried out with a different dog; in the case of one of these tests a dog was used always which previously had never had any contact with a snail grain preparation. It turned out beside, dogs that did not pick up a snail grain preparation offered to them, later ate a different one. The preparations were offered in the morning. If it was noticed in the course of the day that a dog had eaten a snail grain, the remaining material (the entire quantity offered to one dog was 100 gm) was withdrawn.

TABLE 4

The results of repellent tests with perlite and fine bran snail grains

| Variety of snail grain | No. of times offered | No. of times eaten | Intake gm/dog |
| --- | --- | --- | --- |
| Fine bran grain (metaldehyde 6%) | 3 | 3* | 70 70 |
| Perlite grain (metaldehyde 12%) | 7 | 4 | 12 |

Note:
*Dogs that ate a lethal dose.

Despite the high concentration of pesticide on the perlite snail grain, this was hardly eaten any more and if it was eaten, then in such small quantities, that the intake of lethal dose could no longer be noted.

What is claimed is:

1. The pesticide composition for snails comprised of an edible binder, a bait substance for snails, a pesticide for snails, a carrier and an amide having the formula:

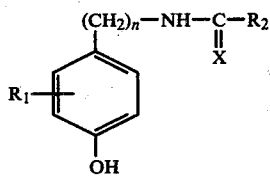

wherein X is an oxygen atom or a sulfur atom, n is 0 or 1, $R_1$ is —OH or —OCH$_3$ and $R_2$ is (i) an alkyl group having 5 to 11 carbon atoms, (ii) an alkylene group having 5 to 11 carbon atoms, (iii) an alkyl group having 5 to 11 carbon atoms and which is substituted with a phenyl group or with a phenyl group that is substituted with one to three alkyl groups, each such alkyl group having one to five carbon atoms, or (iv) an alkylene group having 5 to 11 carbon atoms and which is substituted with a phenyl group or with a phenyl group that is substituted with one to three alkyl groups, each such alkyl group having one to five carbon atoms, said amide being present in an amount between 0.005 and 5 percent by weight, based on the total weight of said pesticide composition, and said carrier being present in an amount between 30 and 70 percent by weight, based on the total weight of said pesticide composition.

2. The pesticide composition for snails as described in claim 1 wherein said edible binder is wheat starch, gum arabic, corn starch or potato starch, wherein said carrier is pumice, fine bran, vermiculite or expanded perlite, wherein said snail bait substance is a commercial feed substance or an aromatic agent which exerts a luring appeal on snails, and wherein said snail pesticide is metaldehyde, copper(II), sulfate, kainite, phenol pentabromide, sodium pentachlorophenolate, 2,4,6-triodophenol or 2,4,6-tribromophenol.

3. The pesticide composition for snails as described in claim 2 wherein said amide is nonyl acid vanillyl amide.

4. The pesticide composition for snails as described in claim 2 wherein said carrier is expanded perlite, and said expanded perlite is present as granules in an amount between 30 and 70 percent by weight based on the total weight of said pesticide composition.

5. The pesticide composition for snails as described in claim 4 wherein said snail pesticide is substantially located on the surface of said expanded perlite and is attached to said surface of said carrier by means of said edible binder.

6. The pesticide composition for snails as described in claim 4 wherein said expanded perlite is in a substantially spheroidal shape having a uniformly rough surface.

7. The pesticide composition for snails as described in claim 2 wherein said edible binder is wheat starch.

8. The pesticide composition for snails as described in claim 2 wherein said snail pesticide is metaldehyde.

9. The pesticide composition of claim 2 wherein said bait substance is a ground grain, a course meal soy bean, a meat meal, a fish meal, a molasses, anise or anise oil.

10. The pesticide composition of claim 2 wherein $R_2$ in said amide is an alkyl group having 5 to 11 carbon atoms.

11. The pesticide composition of claim 10 wherein said carrier is expanded perlite.

12. The pesticide composition of claim 2 wherein $R_2$ in said amide is an alkylene group having 5 to 11 carbon atoms.

13. The pesticide composition of claim 12 wherein said carrier is expanded perlite.

14. The process for the production of a pesticide composition for snails which comprises admixing an amide having the formula:

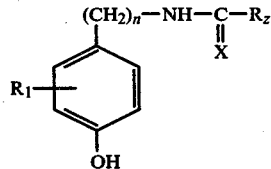

wherein X is an oxygen atom or a sulfur atom, n is 0 or 1, $R_1$ is —OH or —CH$_3$ and $R_2$ is (i) an alkyl group having 5 to 11 carbon atoms, (ii) alkylene group having 5 to 11 carbon atoms, (iii) an alkyl group having 5 to 11 carbon atoms and which is substituted with a phenyl group or with a phenyl group that is substituted with one to three alkyl groups, each such alkyl group having one to five carbon atoms, or (iv) an alkylene group having 5 to 11 carbon atoms and which is substituted with a phenyl group or with a phenyl group that is substituted with one to three alkyl groups, each such alkyl group having one to five carbon atoms, with a snail bait substance, an edible binder, a carrier and a snail pesticide, or applying at least one amide of formula I to the surface of a composition comprised of a snail bait substance and a snail pesticide adhered to a carrier by means of an edible binder, said amide being present in an amount between 0.005 and 5 percent by weight, based on the total weight of said pesticide composition, and said carrier being present in an amount between 30 and 70 percent by weight, based on the total weight of said pesticide composition.

15. The process as described in claim 14 wherein said amide is nonyl acid vanillyl amide.

* * * * *